(12) United States Patent
Flossmann et al.

(10) Patent No.: US 10,987,190 B2
(45) Date of Patent: Apr. 27, 2021

(54) GENERATION OF AUGMENTED REALITY IMAGE OF A MEDICAL DEVICE

(71) Applicant: Brainlab AG, Munich (DE)

(72) Inventors: Sven Flossmann, Feldkirchen (DE); Sebastian Stopp, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 16/604,673

(22) PCT Filed: May 9, 2017

(86) PCT No.: PCT/EP2017/061050
§ 371 (c)(1),
(2) Date: Oct. 11, 2019

(87) PCT Pub. No.: WO2018/206086
PCT Pub. Date: Nov. 15, 2018

(65) Prior Publication Data
US 2020/0078133 A1    Mar. 12, 2020

(51) Int. Cl.
*A61B 90/00* (2016.01)
*A61B 34/20* (2016.01)
(Continued)

(52) U.S. Cl.
CPC .............. *A61B 90/37* (2016.02); *A61B 34/20* (2016.02); *G06T 3/20* (2013.01); *G06T 3/60* (2013.01);
(Continued)

(58) Field of Classification Search
CPC combination set(s) only.
See application file for complete search history.

(56) References Cited

U.S. PATENT DOCUMENTS 6,006,126 A    12/1999   Cosman
8,670,816 B2 *  3/2014   Green ................ A61B 8/0841
                                                    600/424
(Continued)

FOREIGN PATENT DOCUMENTS

WO   WO2007106046 A2   9/2007
WO   WO2007113815 A2   10/2007
(Continued)

OTHER PUBLICATIONS

Drouin, Simon et al., Interaction-Based Registration Correction for Improved Augmented Reality Overlay in Neurosurgery, Montreal Neurological Institute, ResearchGate, Oct. 2015.
(Continued)

*Primary Examiner* — Motilewa Good Johnson
(74) *Attorney, Agent, or Firm* — Middleton Reutlinger (57) ABSTRACT

This document relates to a medical application of augmented reality in which areal image shows a medical device, or at least a part thereof. In an exemplary application, the real image further shows at least a part of a patient's body which is (to be) treated using the medical device. A part of the medical device might not be visible in the real image, for example because it extends into or behind the patient's body. In this case, the virtual image can comprise an augmentation of the medical device, which, for example, represents at least the part of the medical device which is invisible in the real image. This document in particular addresses a correct alignment of the augmentation with the medical device.

14 Claims, 4 Drawing Sheets

(51) Int. Cl.

| | |
|---|---|
| *G06T 7/70* | (2017.01) |
| *G06T 3/20* | (2006.01) |
| *G06T 3/60* | (2006.01) |
| *G06T 7/20* | (2017.01) |
| *G06T 19/00* | (2011.01) |

(52) U.S. Cl.
CPC ............... *G06T 7/20* (2013.01); *G06T 7/70* (2017.01); *G06T 19/006* (2013.01); *A61B 2034/2057* (2016.02); *A61B 2034/2065* (2016.02); *A61B 2090/365* (2016.02); *A61B 2090/371* (2016.02); *A61B 2560/0238* (2013.01); *G06T 2207/10016* (2013.01); *G06T 2207/30004* (2013.01); *G06T 2210/41* (2013.01)

(56) References Cited

U.S. PATENT DOCUMENTS

| | | | |
|---|---|---|---|
| 9,330,502 B2* | 5/2016 | Tuchschmid | G09B 23/30 |
| 9,892,564 B1* | 2/2018 | Cvetko | G06T 19/006 |
| 9,974,615 B2* | 5/2018 | Woerlein | A61B 5/061 |
| 2002/0140694 A1* | 10/2002 | Sauer | G06T 19/006 |
| | | | 345/419 |
| 2003/0029464 A1 | 2/2003 | Chen et al. | |
| 2003/0037449 A1* | 2/2003 | Bani-Hashemi | B25J 9/1689 |
| | | | 33/286 |
| 2004/0238732 A1* | 12/2004 | State | A61B 90/36 |
| | | | 250/250 |
| 2005/0203380 A1 | 9/2005 | Sauer et al. | |
| 2006/0281971 A1* | 12/2006 | Sauer | A61B 34/20 |
| | | | 600/109 |
| 2007/0018975 A1* | 1/2007 | Chuanggui | A61B 90/36 |
| | | | 345/419 |
| 2014/0343404 A1* | 11/2014 | Razzaque | A61B 8/0841 |
| | | | 600/424 |
| 2015/0201892 A1* | 7/2015 | Hummel | A61B 6/12 |
| | | | 348/77 |
| 2015/0287236 A1 | 10/2015 | Winne et al. | |
| 2017/0091939 A1* | 3/2017 | Kluckner | G06T 19/00 |
| 2017/0273715 A1* | 9/2017 | Piron | A61B 34/30 |
| 2018/0071032 A1* | 3/2018 | de Almeida Barreto | A61B 34/20 |
| 2018/0116731 A1* | 5/2018 | State | A61B 34/20 |
| 2018/0125586 A1* | 5/2018 | Sela | H04N 13/204 |

FOREIGN PATENT DOCUMENTS

| | | |
|---|---|---|
| WO | WO2008036050 A2 | 3/2008 |
| WO | WO2018206086 A1 | 11/2018 |

OTHER PUBLICATIONS

Written Opinion and International Search Report for Application PCT/EP2017/061050 dated Aug. 14, 2017.

* cited by examiner

GENERATION OF AUGMENTED REALITY IMAGE OF A MEDICAL DEVICE

TECHNICAL FIELD

The present invention relates to a method for generating an augmented reality image for a medical application in which a real image captured using a camera is combined with a virtual image, wherein the real image comprises a medical device and the virtual image comprises an augmentation of the medical device, and to a corresponding computer program, a computer and a system.

SUMMARY

Augmented reality is a concept which combines a real image captured using a camera with a virtual image to form an augmented reality image. The virtual image typically comprises additional information which enhances the content of the real image.

The present invention is based on a medical application of augmented reality in which the real image shows a medical device, or at least a part thereof. In an exemplary application, the real image further shows at least a part of a patient's body which is (to be) treated using the medical device. A part of the medical device might not be visible in the real image, for example because it extends into or behind the patient's body. In this case, the virtual image can comprise an augmentation of the medical device, which, for example, represents at least the part of the medical device which is invisible in the real image. The virtual image can further comprise augmentations of other objects. Those objects can be other (medical) devices or parts of the patient's body, such as a tumor or (a part of) an organ such as a brain. If the virtual image comprises an augmentation of (a part of) an organ, the interaction between the medical device and the organ, which might not be visible in the real image, becomes visible in the augmented reality image.

Besides organs, augmentations of other structures like vessels or bones or additional information such as highlighting of functional areas, fibers or treatment planning information like screw paths or biopsy paths can be added to the virtual image. Still further, a visualization of treatment planning can be comprised in the virtual image, for example in terms of trajectories or craniotomies.

In order to calculate the augmentation of the medical device, it is necessary to know the relative position of the medical device relative to the camera. The medical device is therefore tracked using, for example, a typical medical tracking system by detecting the positions of markers attached to the medical device. Medical tracking systems are known, for example optical tracking systems operating in the visible or infrared spectrum or electromagnetic tracking systems.

The benefit of the augmented reality image strongly depends on a correct augmentation at least of the medical device, but also of other objects. It is therefore an aim of the present invention to increase the accuracy of the augmentation in the augmented reality image.

The method, the program, the computer and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a method for generating an augmented reality image for a medical application in which a real image captured using a camera is combined with a virtual image, wherein the real image comprises a medical device and the virtual image comprises an augmentation of the medical device. In this document, the term "medical device" can mean the whole medical device or at least a part thereof.

The method involves the step of acquiring camera calibration data representing imaging properties of the camera. A camera typically has an optical system which leads incident light onto an image sensor. The camera calibration data describes how incident light rays are projected onto the image sensor. They represent, for example, the focal distance or geometric distortion of the optical system of the camera. Due to the camera calibration data, it is defined how a virtual object would be imaged by the camera if the virtual object was actually physically present in the real space.

The virtual object can for example be a model of an organ like the brain or a representation of information like planning information or treatment information, which is information of a treatment currently executed on the patient. The virtual object can also be one or more of text or graphics. The virtual object can further represent one or more of a tumor, a vessel, a bone, a functional area and a fiber.

The camera can be any suitable camera, for example a camera of a microscope.

The method further involves the step of tracking the positions of the camera and the medical device. As explained above, the position of an object like the camera or the medical device can, for example, be tracked using a medical tracking system as it is known in the art. The medical tracking systems typically determine the position, which means the location in up to three spatial dimensions and/or the rotational alignment in up to three rotational dimensions, of the object, for example in a reference system of the medical tracking device.

The method further involves the step of calculating a first tracked position of the medical device relative to the camera from the tracked positions of the camera and the medical device. In other words, this step calculates the position of the medical device in a reference system of the camera. If the positions of the camera and the medical device are known in the same reference system, then the relative position between the camera and the medical device can be calculated.

The method further involves the step of performing video tracking of the medical device in the real image, thus obtaining a second tracked position of the medical device relative to the camera. Video tracking identifies an object, like the medical device, in a camera image and determines the position of the object, for example from the shape of the object in the camera image and a model of the object. Details on video tracking can, for example, be found in the article "Vision-based and marker-less surgical tool detection and tracking: A review of the literature" by David Bouget, Max Allan, Danail Stoyanov and Pierre Jannin.

The method according to the present invention therefore determines the position of the medical device relative to the camera twice, once as a first tracked position, for example using a traditional medical tracking system, and once as a second tracked position obtained by video tracking. This means that different tracking modalities are used to determine the first tracked position and the second tracked position.

The medical tracking system can for example be an optical tracking system, an electromagnetic tracking system, a mechanical tracking system or a gyro or accelerometer based tracking system. The tracking system might also use structured light. Another option is inside-out tracking, in which a camera attached to an object to be tracked captures images of markings in its environment.

If both tracking approaches or modalities would give perfect results, the first tracked position and the second tracked position would be identical. However, there are typically differences between the first and the second tracked position. One effect of imperfect tracking using only one tracking approach might be that the medical device in the real image and the augmentation of the medical device in the virtual image are not properly aligned in the augmented reality image.

A tracked position, which means the first tracked position and the second tracked position, is typically given in up to six dimensions, up to three rotational dimensions and up to three translational dimensions. The up to three translational dimensions are orthogonal to each other. The up to three rotational dimensions relate to axes which are orthogonal to each other.

The method therefore further involves the step of calculating the virtual image comprising the augmentation of the medical device from the camera calibration data, the first tracked position of the medical device and the second tracked position of the medical device. As explained above, the camera calibration data is required to imitate the optical properties of the camera.

The first and second tracked positions are used to compensate for imperfections of one tracking method or the other.

In one example, the augmentation of the medical device is calculated from a three-dimensional model of the medical device which is virtually positioned relative to the camera and the augmentation of the medical device is a rendered visualization of the model.

The method further involves the step of generating the augmented reality image by combining the real image and the virtual image. In this step, the augmentation of the medical device, and any other augmentation comprised in the virtual image, is overlaid over the real image.

It shall be noted that the invention equally applies to a stereoscopic real image, which is actually a pair of two two-dimensional images. In this case, a first virtual image is calculated for the first two-dimensional real image and a second virtual image is calculated for the second two-dimensional real image. The first two-dimensional real image is combined with the first virtual image and the second two-dimensional real image is combined with the second virtual image.

Some implementations of video tracking render different visualizations of a model of the medical device for different viewing directions and compare the rendered visualizations with the depiction of the medical object in the real image to find the best matching rendered visualization and thus the corresponding viewing direction, which corresponds to the rotational alignment of the medical object relative to the camera. In one implementation, the rotational alignment comprised in the first tracked position can be used as an initial alignment for the video tracking. The search performed by the video tracking algorithm can then for example be limited to a range around the initial alignment.

In one embodiment, the location of the augmentation of the medical device in the virtual image is based on the second tracked position and the size of the augmentation of the medical device is based on the first tracked position. In this embodiment, the augmentation is, for example, a rendered visualization of the model of the medical device which is then scaled and positioned in the virtual image. Since video tracking typically detects the position of the object in the image plane quite accurately, the distance between the object and the camera might be detected less accurate. It is therefore possible to accurately position the augmentation in the virtual image based on the second tracked position. The depth information, which determines the size of the augmentation in the virtual image, is then taken from the first tracked position. The distance of the medical device to the camera can typically be determined quite accurately using a medical navigation system, in particular if the viewing direction of the medical tracking system is orthogonal to the viewing direction of the camera, or there is at least a large angle between those two viewing directions.

In one embodiment, the augmentation of the medical device is a virtual representation of the medical device, a virtual extension of the medical device or a combination thereof. The virtual representation of the medical device basically shows the medical device, or at least parts thereof, as it is, but, for example, without the markers attached to the medical device. A virtual extension of the medical device does, for example, mean a prolongation of the medical device of a part thereof. If, for example, the medical device is a pointer, a needle or a (rigid) catheter, the virtual extension might represent the path of the pointer, the needle or the catheter if it was moved along its longitudinal axis.

In one embodiment, the augmentation of the medical device comprises a part of the medical device which is invisible in the real image. In this embodiment, the invisible part of the medical device can be made visible in the augmented reality image. This means that, for example, parts of the medical device, which are within or behind the patient's body, can be visualized.

The present invention envisages multiple approaches for calculating the virtual image.

In one approach, calculating the virtual image involves calculating a temporary virtual image including the augmentation of the medical device from the camera calibration data and the first tracked position, modifying the temporary virtual image by shifting it in its image plane based on an difference between the first tracked position and the second tracked position and using the modified temporary virtual image as the virtual image.

In this approach, the whole content of the temporary virtual image is shifted. This means that the same shift is applied to the augmentation of the medical device and any augmentations of other objects. This approach is computationally very effective because only a single two-dimensional shift has to be calculated.

The difference between the first tracked position and the second tracked position is also referred to as position offset. The shift applied when modifying the temporary virtual image is for example represented by a two-dimensional vector parallel to the image plane. This vector is for example calculated from the translational components of the position offset which are parallel to the image plane. In one implementation, the length of this vector further depends on the distance between the camera and the medical object. The distance is for example determined from the first tracked position.

As an equivalent to this approach, no modified temporary virtual image is created, but only a virtual image and this virtual image as shifted or shifted and rotated before or when it is combined with the real image in order to generate the augmented reality image.

In one embodiment, modifying the temporary virtual image also involves a rotation of the temporary virtual image about an axis perpendicular to its image plane. In one implementation, the amount of rotation equals the rotational component of the position offset about an axis perpendicular to the image plane. This embodiment also corrects an imperfection for example of the first tracked position regarding the rotational alignment of the medical device about this axis.

In one approach, a corrected device position of the medical device is calculated from the first tracked position and the second tracked position and the augmentation of the medical device is generated and positioned in the virtual image based on the camera calibration data and the corrected device position.

Compared to the previous approach, this approach does not modify the temporary virtual image, but rather determines a corrected device position and then creates the virtual image based on this corrected device position.

The corrected device position can be calculated as a (weighted) average of the first tracked position and the second tracked position. The same weight can be applied to all dimensions of a respective tracked position or there can be individual weights for each respective dimension. In one implementation, the weights are selected such that the translational dimensions of the corrected device position in directions orthogonal to the viewing direction of the camera are taken from the second tracked position and the translational dimension of the corrected device position along the viewing direction of the camera is taken from the first tracked position.

In one implementation, the rotational dimensions of the corrected device position are taken from the second tracked position. In another implementation, the rotational dimensions of the corrected device position about axes orthogonal to the viewing direction of the camera are taken from the first tracked position and the rotational dimension of the corrected device position about an axis along the viewing direction of the camera is taken from the second tracked position.

In one embodiment, a virtual position of a virtual object is acquired. Then a corrected object position of the virtual object is calculated from the virtual position of the virtual object and a difference between the first tracked position and the second tracked position. Then an augmentation of the virtual object is generated and positioned in the virtual image based on the camera calibration data and the corrected virtual position.

In this embodiment, the position of a virtual object is corrected independently of the position of the medical device and an augmentation of the virtual object in the virtual image depends on the corrected virtual position of the virtual object.

The difference between the first tracked position and the second tracked position is also referred to as position offset. In one implementation, the corrected object position is calculated by adding the position offset to the virtual position of the virtual object. In one example, the dimensions of the position offset might be weighted individually before they are added to the corresponding dimensions of the virtual position of the virtual object.

In this approach, the augmentations of the medical object and any virtual (or other) object directly depend on the corrected position of the medical device or the virtual object, respectively and the camera. The augmentations can then simply be merged to form the virtual image. In particular, the corrected object position of a virtual object is calculated in the same way as the corrected device position, which means that an identified discrepancy between the first tracked position and the second tracked position of the medical object is automatically applied to correct the object position of the virtual object and to thereby create a correct augmentation of the virtual object.

In one approach, the virtual position of a virtual object is acquired and calculating the virtual image involves that the augmentation of the medical device is generated based on the camera calibration data and the first position data, an augmentation of the virtual object is generated based on the camera calibration data and the virtual position of the virtual object and the virtual image is calculated by independently positioning the augmentations of the medical device and the virtual object in the virtual image. In this approach, positioning an augmentation can comprise at least one of locating the augmentation in the virtual image, scaling the augmentation and rotating the augmentation, for example about an axis perpendicular to the image plane of the virtual image.

While the previous approach corrects the measured position of the medical device and the virtual position of the virtual object (if applicable) and then calculates the corresponding augmentations based on the corrected positions, the present approach first calculates the augmentations and then independently positions them in the virtual image. Independently positioning the augmentations of the medical device and the virtual object means that positioning the augmentation of the medical device in the virtual image does not depend on the positioning of the augmentation of the virtual object in the virtual image.

In one embodiment, independently positioning the augmentations involves that the augmentation of the medical device is positioned in the virtual image based on the second tracked position and the augmentation of the virtual object is positioned in the virtual image based on the virtual position of the virtual object and a difference between the first tracked position and the second tracked position.

This means that the augmentation of the medical device solely depends on the first position data, while the positioning of the augmentation in the virtual image solely depends on the second tracked position. However, in a modification of this embodiment, the size of the augmentation may depend on the first tracked position rather than on the second tracked position.

The difference between the first tracked position and the second tracked position is also referred to as position offset. In one implementation, a corrected object position of the virtual object is calculated as explained in the previous approach and the augmentation of the virtual object is positioned in the virtual image depending on the corrected object position.

In the last two approaches, an augmentation of a real object instead of an augmentation of a virtual object can be generated and positioned in the virtual image. In this case, the virtual position of a virtual object is replaced by a tracked position of the real object. The tracked position is for example acquired using the same tracking system that is used for determining the positions of a camera and the medical device.

A virtual position of a virtual object represents for example the position of the virtual object relative to the camera.

The real object can for example be another medical device or (a part of) a patient's body. If the virtual object represents a structure in a patient's body, then the position of the patient's body, or the part thereof in which the structure is located, may be tracked and the virtual position may be calculated from the tracked position of the patient's body and the known position of the structure within the patient's body. The position of the structure within the patient's body might be obtained by analyzing a medical image of the patient, such as an X-ray image, a CT image or an MRT/MRI image.

In the present invention, there are two equivalent understandings if the virtual image shall comprise a depiction of a structure, like an organ or a tumor, of a patient's body. In one understanding, the patient is a real object and the depiction is an augmentation of the real object. The augmentation is for example generated from a model or a three-dimensional image of the structure. In the other understanding, the model or the three-dimensional image is a virtual object and the depiction is an augmentation generated from the model or the three-dimensional image.

The three approaches mentioned above are different in how the virtual image is generated and/or combined with the real image. However, common to all approaches is the use of both the first tracked position and the second tracked position.

In one embodiment, the method further involves performing additional video tracking of a real object. There are thus a first tracked position and a second tracked position of the object. This enables a fully independent correction of the position of the object relative to the camera or positioning of the augmentation of the object in the virtual image.

In one embodiment of the invention, the first tracked position has associated a first confidence value, the second tracked position has associated a second confidence value and calculating the virtual image is based on the first confidence value and the second confidence value. A confidence value for example represents the quality of a tracked position. Calculating the virtual image for example utilizes the best combined quality of the first tracked position and the second tracked position. The higher a confidence value, the higher the quality, or accuracy, of the corresponding tracked position.

In one implementation, calculating the virtual image is based on the first tracked position if the first confidence value is above a first threshold and calculating the virtual image is based on the second tracked position if the second confidence value is above a second threshold. If both confidence values are above their respective thresholds, calculating the virtual image may be based on both the first tracked position and the second tracked position in common or based on the one of the first and second tracked position having the higher confidence value.

There can be a single confidence value for a tracked position or there can be individual confidence values for each dimension of a tracked position. In one implementation, the dimensions of a tracked position for which the confidence value is above a corresponding threshold is used for calculating the virtual image. If, for a particular dimension, the corresponding first confidence value of the first tracked position and second confidence value of the second tracked position is below the respective threshold, the dimension of the tracked position which has the higher confidence value out of the first and second tracked positions may be utilized.

A confidence value may depend on knowledge about the tracking technology. For optical tracking using a stereoscopic camera, the quality of the depth information, which means the distance to the tracking camera along the viewing direction of the tracking camera, is typically rather low. So if video tracking is assumed to obtain better results in this dimension, the corresponding second confidence value of the second tracked position is set to be higher than the corresponding first confidence value of the first tracked position.

The confidence values of the two tracked positions may depend on the geometry of the medical device and the attached markers. If there is a device with for example four markers with a large distance among each other and a part of interest of the medical device, such as the tip of a pointer, is close to the markers, then the confidence in the first tracked position obtained using an optical tracking system would be very high. To the contrary, in the example of a stylet, the markers are close to each other and the part of interest of the medical device is far away from the markers. The confidence in the first tracked position obtained by an optical tracking system is thus low. So if the stylet, or for example the tip of the stylet, is visible in the real image, the second confidence value of the second tracked position may be set high.

Further, there can be a dynamic adaptation of the confidence values. Measurement noise can be used for determining the quality of the rout mean square of the corresponding medical device in a particular position, which means how good the known geometry of the markers can be fitted to the measured position of the single markers. The first confidence value can then be adapted accordingly.

The present invention further relates to a program which, when running on a computer, causes the computer to perform the method described herein and/or to a program storage medium on which the program is stored, in particular in a non-transitory form. The invention further relates to a computer on which said program is stored and/or run.

Still further, the present invention relates to a system comprising a trackable camera, a medical tracking system for tracking the camera and a medical device and the above computer.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The invention can be used for microscopes and/or augmented reality related applications in the applicant's Image Guided Surgery products, providing a better and more accurate visualization and tracking information.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
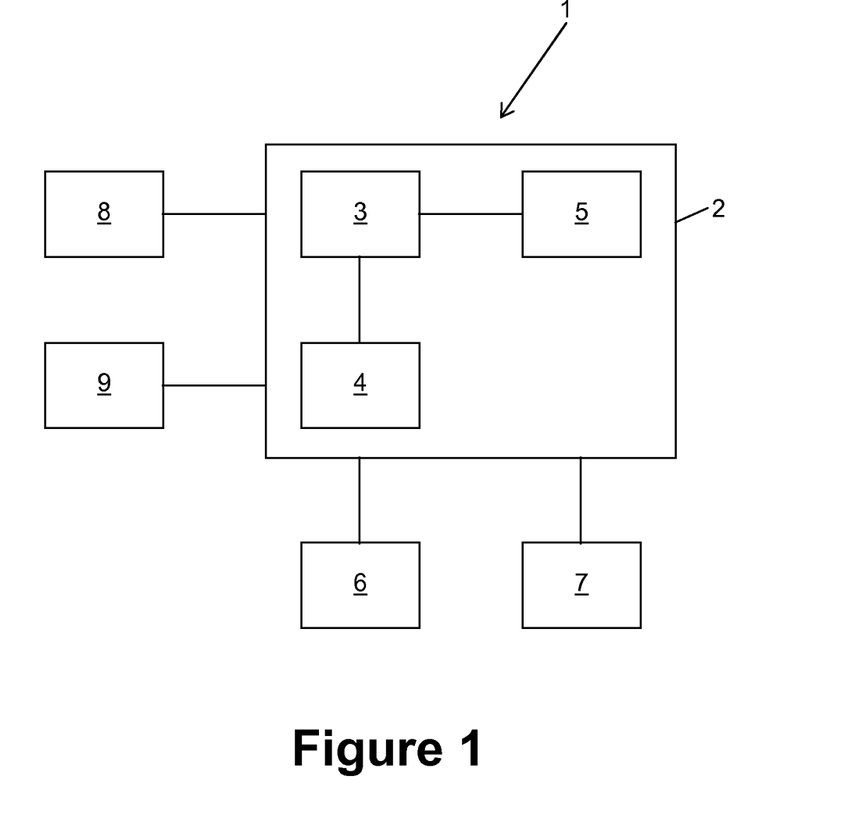
FIG. 1 a system for generating an augmented reality image,
FIG. 2 a setup in which the present invention is used,
FIG. 3a a real image,
FIG. 3b a virtual image,
FIG. 3c an augmented reality image and
FIG. 4 a flow diagram of the present invention.

FIG. 1 schematically shows a system 1 for generating an augmented reality image for a medical application. The system 1 comprises a computer 2 having a central processing unit (CPU) 3, an interface 4 and a memory 5. The computer 2 is connected to an input device 6, an output device 7, a tracking system 8 and a video camera 9. The input device 6 is optional and comprises for example at least one of a keyboard, a mouse, a track ball and a touch-sensitive surface. The output device 7 is for example a monitor or a projector, but can also be a head mounted display, such as Google Glass®, Samsung Gear VR® or Oculus Rift®. Some or all components of the computer 2 can be integrated into the head mounted display.

The central processing unit 3 is configured to execute code which implements the present invention. The code is for example stored in the memory 5. This memory 5 further stores data to be processed and/or processed data. The interface 4 connects the computer 2 to at least one of the input device 6, the output device 7, the tracking system 8 and the video camera 9.

The tracking system 8 can be a complete tracking system which delivers position information to the computer 2. As an alternative, the tracking system 8 only comprises a detector, such as an EM-detector or a stereoscopic camera, and the data processing part which analyses the output of the detector is comprised in the computer 2.

Figure 2:
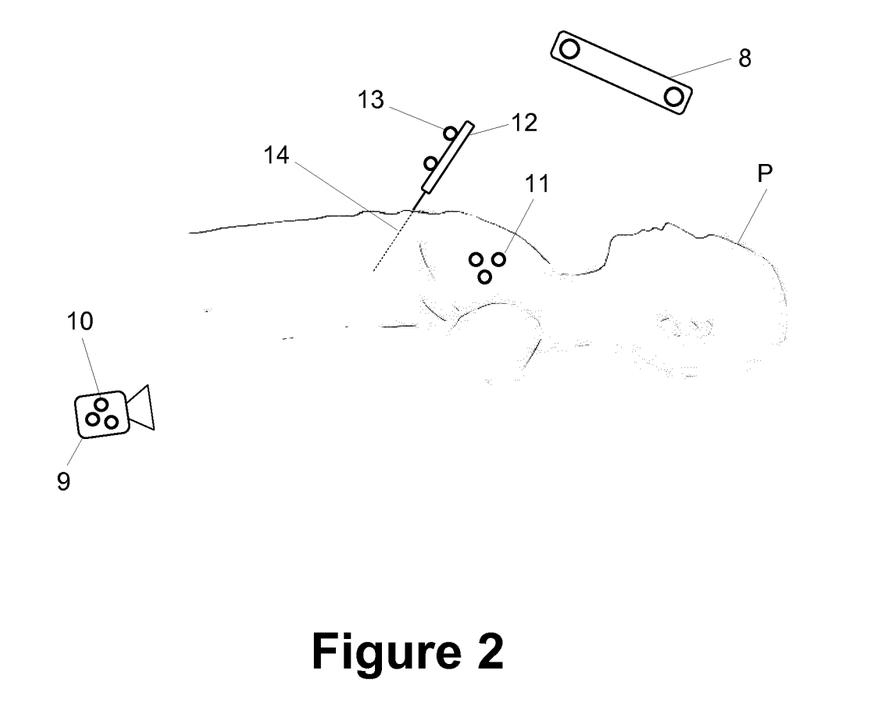

FIG. 2 shows a scenario in which the present invention can be used. The video camera 9 captures a real image showing a part of a patient P and a part of a navigated pointer 12. Markers 11 are attached to the patient P, markers 10 are attached to the video camera 9 and markers 13 are attached to the navigated pointer 12, which is an example of a medical device. The stereoscopic camera of the tracking system 8 captures stereoscopic images of the markers 10, 11, 13. The markers are identified in the output images of the stereoscopic camera in order to localize the markers in a reference of the tracking system 8. The tracking system 8 can therefore determine the positions of the video camera 9, the pointer 12 and the patient P from the positions of the markers 9, 11 and 13, respectively.

Figure 3A:
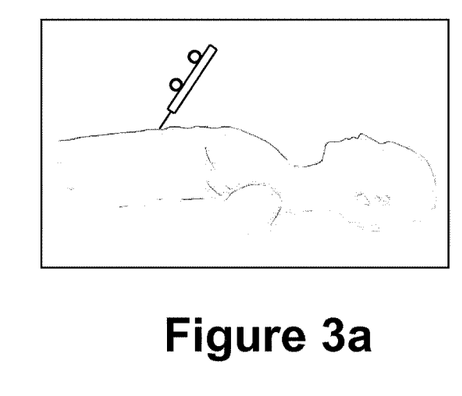

FIG. 3a shows an exemplary real image captured by the video camera 9. The real image depicts a part of the patient P and a part of the pointer 12, wherein the tip of the pointer 12 is hidden behind the patient P and therefore not visible in the real image.

Figure 3B:
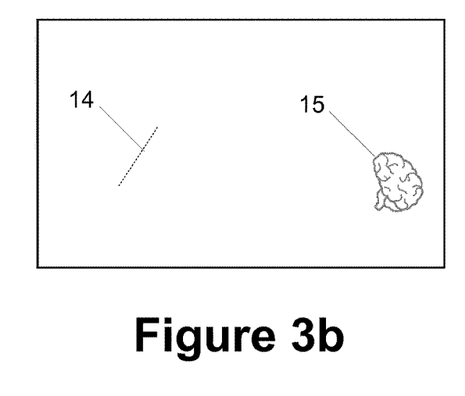

Augmented reality can supplement the real image with additional information. This is achieved by combining the real image with a virtual image which comprises augmentations of objects. An exemplary virtual image is shown in FIG. 3B. The augmentation 14 of the pointer 12 is an extension of the pointer 12. In particular, the augmentation 14 represents the part of the pointer 12 which is hidden behind the patient P. However, the augmentation 14 could also represent more or all of the pointer 12.

The virtual image further comprises an augmentation 15 of the patient's brain. A model of the brain, which is also referred to as brain model, can be understood as a virtual object which is to be placed in the virtual image. The virtual object has assigned thereto a virtual position, which corresponds to the position of the patient's brain relative to the patient. From another point of view, the patient P is an object and the visualization of the patient's brain in the virtual image is an augmentation of the patient. Both interpretations have the same result that the brain of the patient P, which is not visible in the real image, becomes visible in the virtual image.

Figure 3C:
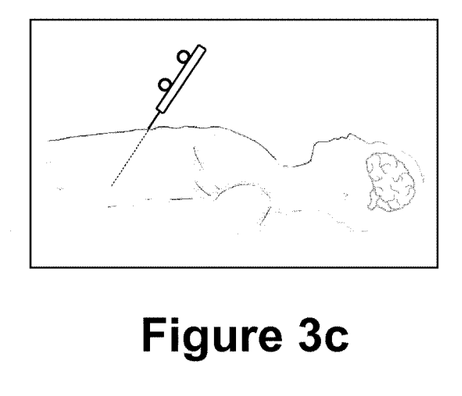

FIG. 3c shows an augmented reality image which is a combination of the real image of FIG. 3a and the virtual image of FIG. 3b.

In general, an augmentation of an object, such as a medical device like the pointer 12, a structure of the patient's body or any other object, is calculated by virtually placing the object in front of the video camera 9 and calculating a visualization of the object as it would be output by the video camera 9 if the object was actually present in front of the video camera 9. This visualization is typically rendered, for example using ray-tracing technologies and the optical properties of the video camera 9. The optical properties of the video camera 9 in particular describe distortions caused by the optical system of the video camera 9. In particular, the part of light emitted from each one out of a plurality of points on the surface of the object passing through the optical system of the video camera 9 and falling onto one or more pixels of the image detector of the video camera 9 are traced in order to render the augmentation. The augmentation therefore depends on the properties of the video camera 9 and the position of the object relative to the video camera.

This relative position between the video camera 9 and the object is determined as follows with example of the pointer 12.

The navigation system 8 determines the position of the video camera 9 in a reference system of the tracking system 8 by determining the positions of the markers 10 attached to the video camera 9 and from the known (registered) locations of the markers 10 relative to the video camera 9. In analogy, the tracking system 8 determines the position of the pointer 12 in the reference system of the navigation system 8 by measuring the locations of the markers 13 attached to the pointer 12 and from the known (registered) locations of the markers 13 on the pointer 12. Once the positions of the video camera 9 and the pointer 12 are known in the reference system of the tracking system 8, the position of the pointer 12 relative to the video camera 9 can be calculated therefrom.

An issue with this approach is that positions measured using a tracking system are typically not absolutely correct, for example due to a limited resolution of the tracking system or noise in the detected signal. This means that the position of an object relative to the video camera 9 might not be absolutely correct, which means that the augmentations in the virtual image might not properly align with the corresponding objects in the real image. This issue is addressed by the present invention.

Figure 4:
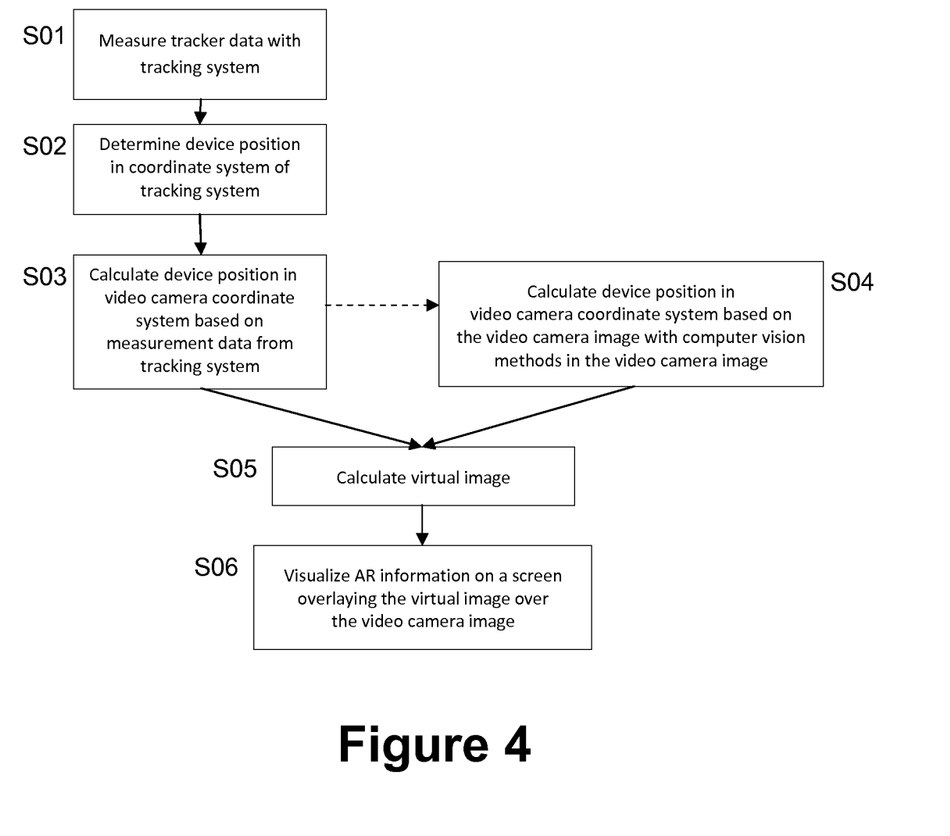

FIG. 4 shows an exemplary flow chart of the present invention. The following explanation covers a scenario in which the virtual image comprises an augmentation of a virtual object. The virtual object is a model of the brain of the patient P.

In step S01, the positions of the video camera 9, the pointer 12 and the patient P are tracked using the tracking system 8. In step S02, the position of the video camera 9 is calculated from the position of the markers 10 and the position of the pointer 12 is calculated from the locations of the markers 13. In addition, the virtual position of the model of the brain is calculated from the locations of the markers 11. The positions of the video camera 9 and the pointer 12 as well as the virtual position of the brain model are thus given in the coordinate system of the tracking system 8. In step S03, those positions are converted into relative positions between the video camera 9 on the one hand and the pointer 12 and the brain model, respectively on the other hand. The relative position between the pointer 12 and the video camera 9 is referred to as the first tracked position of the pointer 12.

In step S04, video tracking of the pointer 12 is performed in the real image captured by the video camera 9. The result is the second tracked position of the pointer 12 relative to the video camera 9. Video tracking in step S04 optionally utilizes the first tracked position of the pointer 12 calculated in step S03 as an initial position for the tracking. This might improve and/or accelerate the video tracking.

In step S05, the virtual image is calculated from camera calibration data representing imaging properties of the video camera 9, the first tracked position of the pointer 12, the second tracked position of the pointer 12 and the virtual position of the brain model.

In particular, a model of the pointer 12 is virtually positioned in front of the video camera 9 and the augmentation 14 of the pointer 12 is calculated from a model of the pointer 12 and added to the virtual image. In analogy, the augmentation 15 of the brain model is calculated from the brain model and added to the virtual image.

In step S06, an augmented reality image is generated by combining the real image and the virtual image and is then displayed on the output device 7.

Different options for calculating the virtual image in step S05 will now be described.

An first option, the virtual image is calculated and the whole virtual image is shifted relative to the real image such that the pointer 12 and the augmentation 14 are properly aligned. This may also involve a rotation of the virtual image about an axis perpendicular to the image plane.

In one implementation, the augmentation 14 of the pointer 12 is calculated based on the first tracked position, but not from the second tracked position. The location of the augmentation 14 in the virtual image also depends on the first tracked position. The augmentation 15 of the brain model is calculated and positioned in the virtual image based on the virtual position. The virtual image is then shifted or shifted and rotated depending on the offset between the first tracked position and the second tracked position.

In this first option, the whole virtual image is shifted or shifted and rotated. The augmentation 15 is therefore modified at the same time, such that it is not necessary to treat it separately.

In a second option, the augmentation 14 of the pointer 12 and the augmentation 15 of the brain model are calculated based on the first tracked position and the virtual position, respectively as described above, but are positioned independently in the virtual image. The size of the augmentation 14 may depend on the first tracked position. This means that only the augmentation 14 and not the complete virtual image is shifted or shifted and rotated as explained above. The shift or shift and rotation of the augmentation 15 is then calculated separately.

In one implementation, the shift of the augmentation 15 equals the shift of the augmentation 14 multiplied by the distance between the video camera 9 and the brain model divided by the distance between the video camera 9 and the pointer 12. This addresses that the shift is distance dependent.

In another implementation, a video marker is attached to the patient P and video tracked in the real image output by the video camera 9. With the known positional relationship between the video marker and the brain, a tracked position of the brain model as the virtual object is determined. The augmentation 15 of the brain model can therefore be generated and positioned in the virtual image depending on the virtual position of the brain model and the tracked position of the brain model in analogy to the calculations regarding the augmentation 14 of the pointer 12 using the first and second tracked positions thereof.

In a third option, the position of the video camera 9 tracked using the tracking system 8 is corrected by an offset representing the difference between the first tracked position and the second tracked position of the pointer 12. The corrected position of the video camera 9 is used to calculate the relative positions between the video camera 9 on the one hand and the pointer 12 and the brain model, respectively on the other hand. As an alternative, the relative positions of the pointer 12 and the brain model can be corrected using this offset. The augmentations 14 and 15 are then calculated from the corrected relative position of the pointer 12 and the brain model, respectively.

Step S05 might further comprise deciding which information is used to calculate a relative position between the video camera 9 and an object, that is a medical device like the pointer 12, another real object or a virtual object. Taking the pointer 12 as an example, its position relative to the video camera 12 can be calculated from the first tracked position, the second tracked position or a combination thereof. In particular, different dimensions of the first and second tracked positions might have different reliability values, for example depending on the geometry of the markers 13, the pointer 12 and the setup of the video camera 9, the tracking system 8 and the pointer 12. So if, for example, the stereoscopic camera of the tracking system 8 cannot see the pointers 13, the augmentation 14 of the pointer 12 is generated and positioned solely depending on the second tracked position.

In analogy, a similar decision can be made for other objects.

The invention claimed is:

1. A method for generating an augmented reality image in which a real image captured using a camera is combined with a virtual image, wherein the real image includes a medical device and the virtual image includes an augmentation of the medical device, comprising:
    acquiring camera calibration data indicative of a projection of incident light ray onto an image sensor of the camera;
    tracking a first position of the camera and a first position of the medical device;
    calculating a first tracked position of the medical device relative to the camera from the tracked first positions of the camera and the medical device;
    performing video tracking of the medical device in the real image, thereby obtaining a second tracked position of the medical device relative to the camera;
    calculating the virtual image comprising the augmentation of the medical device from the camera calibration data, the first tracked position of the medical device and the second tracked position of the medical device;
    generating the augmented reality image by combining the real image and the virtual image; and
    preparing for output on a display device the augmented reality image.

2. The method of claim 1, wherein the location of the augmentation of the medical device in the virtual image is based on the second tracked position and the size of the augmentation of the medical device is based on the first tracked position.

3. The method of claim 1, wherein the augmentation of the medical device is a virtual representation of the medical device, a virtual extension of the medical device or a combination thereof.

4. The method of claim 3, wherein the augmentation of the medical device comprises a part of the medical device which is invisible in the real image.

5. The method of claim 1, wherein calculating the virtual image includes
    calculating a temporary virtual image including the augmentation of the medical device from the camera calibration data and the first tracked position;
    modifying the temporary virtual image by shifting it in its image plane based on a difference between the first tracked position and the second tracked position to create a modified temporary virtual image; and
    using the modified temporary virtual image as the virtual image.

6. The method of claim 5, wherein modifying the temporary virtual image also involves a rotation of the temporary virtual image about an axis perpendicular to its image plane.

7. The method of claim 1, wherein:
    a corrected device position of the medical device is calculated from the first tracked position and the second tracked position; and
    the augmentation of the medical device is generated and positioned in the virtual image based on the camera calibration data and the corrected device position.

8. The method of claim 7, wherein:
    a virtual position of a virtual object is acquired;
    a corrected object position of the virtual object is calculated from the virtual position of the virtual object and a difference between the first tracked position and the second tracked position;
    an augmentation of the virtual object is generated and positioned in the virtual image based on the camera calibration data and the corrected virtual position.

9. The method of claim 1, wherein a virtual position of a virtual object is acquired and calculating the virtual image includes:
    generating the augmentation of the medical device based on the camera calibration data and the first position data;
    generating an augmentation of the virtual object based on the camera calibration data and the virtual position of the virtual object; and
    calculating the virtual image by independently positioning the augmentations of the medical device and the virtual object in the virtual image.

10. The method of claim 9, wherein independently positioning the augmentations includes:
    positioning the augmentation of the medical device in the virtual image based on the second tracked position; and
    positioning the augmentation of the virtual object in the virtual image based on the virtual position of the virtual object and a difference between the first tracked position and the second tracked position.

11. The method of claim 1, wherein the first tracked position has associated a first confidence value, the second tracked position has associated a second confidence value and calculating the virtual image is based on the first confidence value and the second confidence value.

12. The method of claim 11, wherein calculating the virtual image is based on the first tracked position if the first confidence value meets a first threshold and calculating the virtual image is based on the second tracked position if the second confidence value meets a second threshold.

13. At least one non-transitory computer readable storage medium comprising instructions that, in response to execution of the instructions by one or more processors, cause the one or more processors to perform the following operations for generating an augmented reality image in which a real image captured using a camera is combined with a virtual image, wherein the real image includes a medical device and the virtual image includes an augmentation of the medical device, the instructions operable to:
    acquire camera calibration data indicative of a projection of incident light ray onto an image sensor of the camera;
    track a first position of the camera and a first position of the medical device;
    calculate a first tracked position of the medical device relative to the camera from the tracked first positions of the camera and the medical device;
    perform video tracking of the medical device in the real image thereby obtaining a second tracked position of the medical device relative to the camera;
    calculate the virtual image comprising the augmentation of the medical device from the camera calibration data, the first tracked position of the medical device and the second tracked position of the medical device;
    generate the augmented reality image by combining the real image and the virtual image; and
    prepare for output on a display device the augmented reality image.

14. A system, comprising:
    a trackable camera;
    a medical tracking system for tracking the camera and a medical device;
    at least one computer having at least one processor having associated memory, the memory storing instructions which when executed by the at least one processor, cause the at least one processor to:

acquire camera calibration data indicative of a projection of incident light ray onto an image sensor of the camera;

track a first position of the camera and a first position of the medical device;

calculate a first tracked position of the medical device relative to the camera from the tracked first positions of the camera and the medical device;

perform video tracking of the medical device in a real image thereby obtaining a second tracked position of the medical device relative to the camera;

calculate a virtual image comprising an augmentation of the medical device from the camera calibration data, the first tracked position of the medical device and the second tracked position of the medical device;

generate an augmented reality image by combining the real image and the virtual image.

* * * * *